(12) United States Patent
Scheremet et al.

(10) Patent No.: US 8,309,786 B2
(45) Date of Patent: Nov. 13, 2012

(54) LOW PROFILE THORACIC WOUND SEAL WITH LATERALLY-DIRECTED DISCHARGE

(75) Inventors: William Scheremet, Hinckley, MN (US); Steven J. Brinkman, Eden Prairie, MN (US); Kim A. Jacobsen, Minneapolis, MN (US)

(73) Assignee: FastTrack Medical Solutions LLC, Eden Prairie, MN (US)

( * ) Notice: Subject to any disclaimer, the term of this patent is extended or adjusted under 35 U.S.C. 154(b) by 338 days.

(21) Appl. No.: 12/857,522

(22) Filed: Aug. 16, 2010

(65) Prior Publication Data

US 2012/0041353 A1   Feb. 16, 2012

(51) Int. Cl.
*A61F 13/00* (2006.01)
(52) U.S. Cl. ............................................ 602/43; 602/48
(58) Field of Classification Search .............. 602/42–59; 604/122; 128/888, 889; 73/866.4
See application file for complete search history.

(56) References Cited

U.S. PATENT DOCUMENTS

| | | | |
|---|---|---|---|
| 3,954,105 A | 5/1976 | Nordby et al. | |
| 4,465,062 A | 8/1984 | Versaggi et al. | |
| 4,717,382 A | 1/1988 | Clemens et al. | |
| 5,160,322 A | 11/1992 | Scheremet et al. | |
| 5,431,633 A * | 7/1995 | Fury | 604/122 |
| 5,478,333 A | 12/1995 | Asherman, Jr. | |
| 5,520,632 A * | 5/1996 | Leveen et al. | 604/9 |
| 6,629,469 B2 * | 10/2003 | Jaszczak et al. | 73/866.4 |
| 6,843,145 B2 * | 1/2005 | Jaszczak et al. | 73/866.4 |
| 7,504,549 B2 | 3/2009 | Castellani et al. | |
| 7,615,674 B2 | 11/2009 | Asherman | |
| 2007/0232978 A1 | 10/2007 | Castellani | |
| 2008/0033377 A1 | 2/2008 | Kauth et al. | |
| 2008/0091152 A1 | 4/2008 | Asherman | |
| 2008/0178884 A1 | 7/2008 | Gerson et al. | |
| 2008/0234726 A1 | 9/2008 | Biddle et al. | |

FOREIGN PATENT DOCUMENTS

| | | |
|---|---|---|
| AU | 1587692 A1 | 10/1992 |
| CA | 2104966 | 8/1992 |
| EP | 0596889 | 5/1994 |
| WO | WO9215344 | 9/1992 |

* cited by examiner

*Primary Examiner* — Michael A. Brown
(74) *Attorney, Agent, or Firm* — Thompson Patent Law Offices PC

(57) ABSTRACT

Apparatus and associated methods for a wound valve assembly provide an annular space extending radially around a central portion of a valve, which valve acts to substantially relieve pressure build up in a thoracic cavity when applied to a thoracic wound. In an illustrative example, the valve assembly may form an annular space that extends radially in all directions around a check valve. In some examples, gasses and exudates may flow substantially radially and/or parallel to the patient's local body. Various embodiments may advantageously provide open fluid communication for the gasses and exudates escaping from the wound when the valve assembly is partially covered (e.g., body armor, clothing, blankets), or when the patient may be laying down on the side of the body with the wound, for example.

20 Claims, 6 Drawing Sheets

LOW PROFILE THORACIC WOUND SEAL WITH LATERALLY-DIRECTED DISCHARGE

TECHNICAL FIELD

Various embodiments relate generally to apparatus or methods for sealing thoracic wounds while relieving pressure build-up in a thoracic cavity.

BACKGROUND

In the event of a serious injury, it often falls to the first responders to quickly stabilize a patient for transport to an appropriately equipped medical care facility. The first responders are often trained to assess patients' injuries. They may often be required to determine appropriate procedures to quickly stabilize a traumatic injury, and to determine what their limitations may be in terms of time to treat before transport in view of the criticality of the patient's wounds.

One type of serious injury that may be encountered as a result of, for example, a military encounter, is a bullet or knife wound. In the event of a gunshot or knife wound penetrating the chest or thoracic region, for example, a first responder may be equipped to apply a dressing over the wound. Punctures that penetrate the thoracic wall, however, are serious and demand immediate medical attention. Without access to a well equipped medical facility, there is a danger that a patient can develop a life-threatening condition, such as pneumothorax, if pressure is allowed to build up in the pleural space through the wound.

SUMMARY

Apparatus and associated methods for a wound valve assembly provide an annular space extending radially around a central portion of a valve, which valve acts to substantially relieve pressure build up in a thoracic cavity when applied to a thoracic wound. In an illustrative example, the valve assembly may form an annular space that extends radially in all directions around a check valve. In some examples, gasses and exudates may flow substantially radially and/or parallel to the patient's local body. Various embodiments may advantageously provide open fluid communication for the gasses and exudates escaping from the wound when the valve assembly is partially covered (e.g., by body armor, clothing, blankets), or when the patient may be laying down on the side of the body with the wound, for example.

Various embodiments may achieve one or more advantages. For example, some embodiments may provide an annular volume which may be maintained to provide fluid communication to discharge fluid pressure build up in the presence of clothing, blankets, body armor, or when laying on the side of the wound dressing assembly. Some embodiments of the valve may provide optical magnification to more easily inspect a check valve and to verify proper valve operation. Some embodiments may include a color-tinted valve membrane (e.g., yellow) which may substantially contrast with typical exudates (e.g., including blood) to further simplify the inspection and verification of valve operation. Various embodiments may include interference fit mechanisms for assembling the valve subcomponents to a soft pliable carrier (e.g., dressing bandage) to form a wound seal system. The carrier may provide a pliable, soft substrate for an aggressive hydrogel combined with an antimicrobial, whereby the combined assembly does not readily form channels that could break a seal of the valve against the patient, thereby providing an undesirable flow communication for allowing pressure build up in the pleural cavity, for example. As a further example, some embodiments may incorporate a hydrogel combined with an antimicrobial to releasably adhere the valve assembly to the patient, and to permit the immediate and direct application of the valve assembly to protect against pressure build up from an open thoracic wound in the field, for example.

The details of various embodiments are set forth in the accompanying drawings and the description below. Other features and advantages will be apparent from the description and drawings, and from the claims.

BRIEF DESCRIPTION OF THE DRAWINGS

Like reference symbols in the various drawings indicate like elements.

DETAILED DESCRIPTION OF ILLUSTRATIVE EMBODIMENTS

FIGS. 1A-1D depict perspective, cross-sectional, plan, and elevation views of an exemplary valve assembly. In the depicted FIG. 1A, a low profile valve assembly 100 is positionable over a wound to limit pressure build-up in the thoracic cavity, for example. As will be described, the valve assembly 100 is configured for assembly to a soft, pliable carrier (not shown) that forms a substantially air-tight seal to the skin around the wound by virtue of an adhesive coating (e.g., hydrogel) on one surface of the carrier substrate (examples of which are described in further detail with reference to FIGS. 3 and 7). For purposes of clearly introducing embodiments of the valve assembly 100, the valve assembly 100 is shown without a carrier layer in FIGS. 1-2.

Figure 1A:
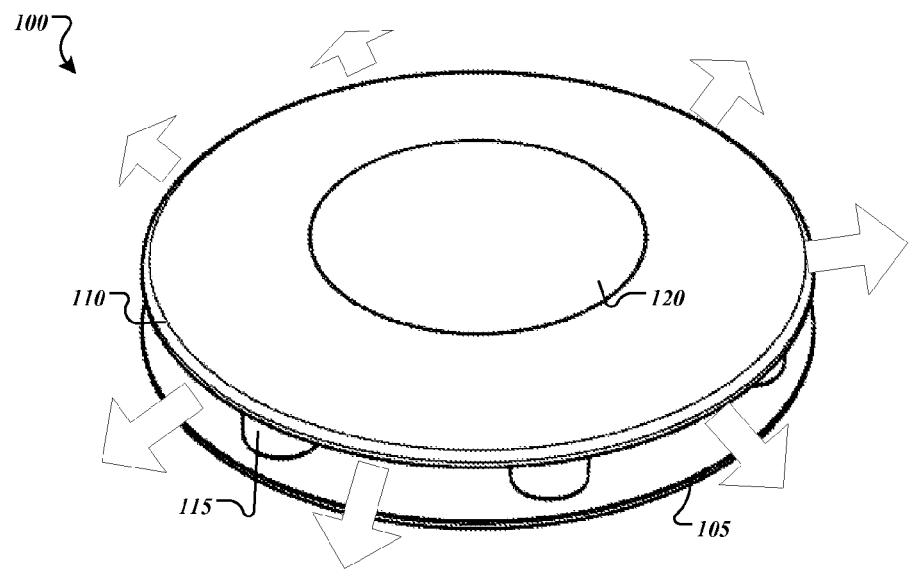
FIGS. 1A-1D depict perspective, cross-sectional, plan, and elevation views of an exemplary valve assembly.

In particular examples, the valve assembly 100 may provide for radial discharge of gasses (e.g., air) and/or exudates (e.g., blood) that may flow out of a thoracic wound. The arrows in the FIG. 1A depict lateral flow paths for communicating fluids (e.g., blood, gasses, or other exudates) radially away from the wound. The various flow paths permit lateral fluid flow in a plane substantially parallel to a plane tangent to the patient's body at the wound site. In some examples, substantially lateral and radial flow paths may substantially reduce the risk that all the flow paths will be occluded by materials (e.g., such as clothing, blankets, body armor) or when the patient is lying on the side of the body with the valve assembly 100. In an illustrative example, a patient may be treated with two valve assemblies 100, one on a front entry thoracic wound and one on a rear exit thoracic wound, and the patient may need to lie down on the back during transport, for example.

The valve assembly 100 includes a bottom housing 105 and a top housing 110. The housings 105, 100 each include an annular flange lying in substantially parallel planes. Between the facing surfaces of the respective annular flanges are a number of support bosses 115. The support bosses 115 are disposed in a volume between the annular flanges of the housing 105, 110 that form an annular cavity to permit lateral fluid flow discharge from the valve assembly 100 (see exemplary arrows).

In this embodiment, the top housing 110 further includes an optical gain element, a lens 120, configured to magnify a view of an interior operation of the valve assembly. In particular examples, the lens may enhance an image of the valve operation, to permit an attending care provider, to monitor operation of a unidirectional valve, for example. Operations of exemplary valves will be described in further detail, for example, with reference to FIGS. 2-6.

Figure 1B:
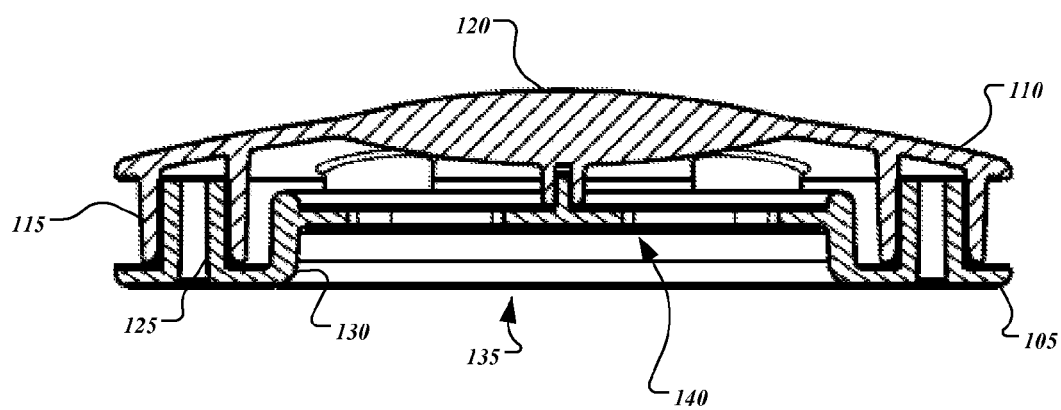
Figure 1C:
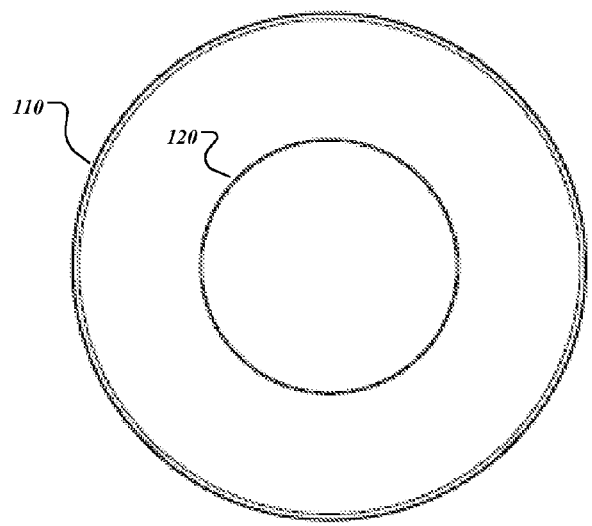
Figure 1D:
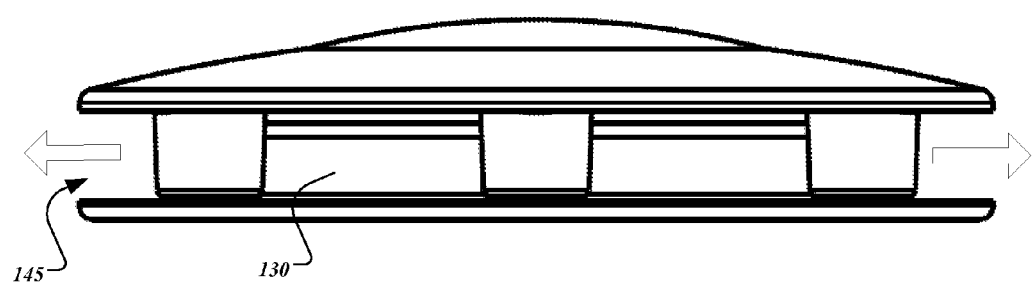

FIG. 1B-1D show cross-section, top, and plan views that reveals further detail of the exemplary valve assembly 100 of FIG. 1A. The bottom housing 105 further includes support pins 125 that correspond to the support bosses 115. When registered in alignment and assembled, each of the support pins 125 provide an interference fit to engage an interior of a corresponding one of the support bosses 115. The coupling of the support pins 125 to the support bosses 115 further engage a carrier (not shown in this figure). The support pins 25, being covered by the carrier, drive a local portion of the carrier material web into the support bosses 215, thereby securely engaging the carrier to the assembled bottom and top housings 105, 110.

The bottom housing 105 further includes a central frame 130, which defines a bottom aperture 135 through which fluids pass through a valve system 140 and then discharge laterally through an annular cavity 145 (see FIG. 1D).

In the depicted example, a bottom portion of the lens 120 includes a boss to engage and couple to a projection of the valve system. This coupling may, in some embodiments, secure the valve membrane to the membrane mounting pin, as will be described in further detail with reference to FIGS. 2A-2B.

The lens 120 is depicted, as an example, with a variable thickness profile such that, according to the relative indices of refraction, an observer can view an image of the interior of the valve assembly with the benefit of a magnification factor. In some implementations, this may advantageously permit closer inspection of the small movements and small quantities of materials in the valve system 140. The lens 120 portion may be a substantially transparent plastic or glass material. In some examples, the lens 120 may be made of a substantially different material (e.g., glass, high density polyethylene) than the remainder of the top housing 110 (e.g., polypropylene). In some embodiments, the lens 120 may be formed from materials arranged to provide a graded index of refraction (GRIN) to yield an optical gain or magnification.

Figure 2A:
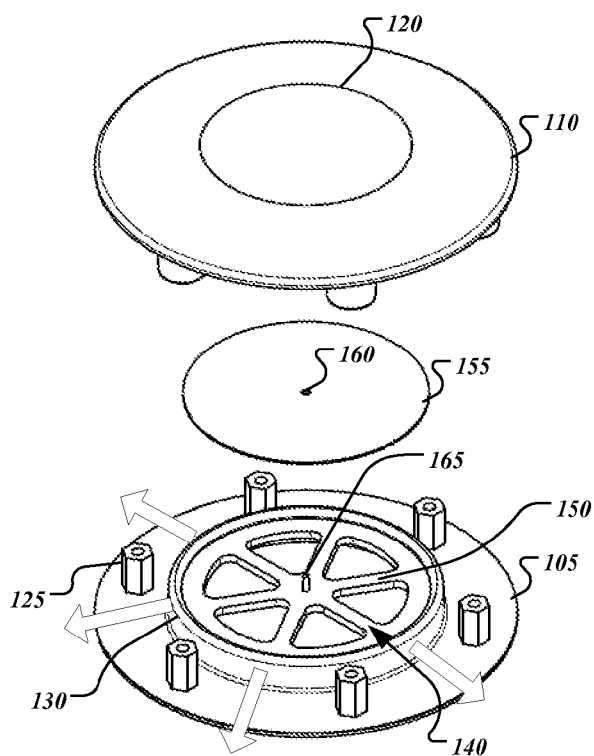
FIGS. 2A-2B depict exploded perspective views of the example of FIGS. 1A-1D.
Figure 2B:
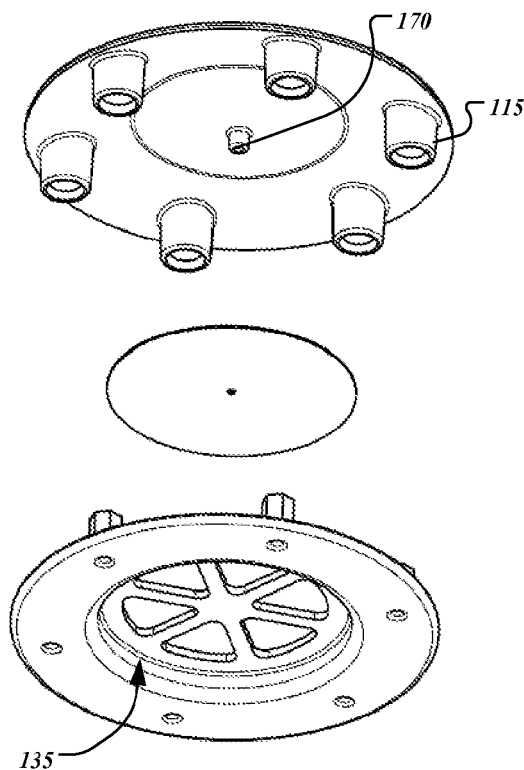

FIGS. 2A-2B depict exploded perspective views of the example of FIGS. 1A-1D. FIG. 2A shows an exemplary embodiment of an interior of the valve system 140. In particular, the central frame 130 further includes a membrane support member 150 arranged as a number of spokes formed between a peripheral ring and a central hub. In the depicted embodiment, a valve membrane 155 is sized to lie on the membrane support member 150 within the upward extending wall of the central frame 130. The central hub of the central frame 130 includes a mounting pin 165 to register and locate the mount aperture 160 of the valve membrane 155.

The bottom housing 105 and the top housing 110 may extend radially from a central axis along which the mounting pin 165 is aligned. In some embodiments, a ratio of a radius to the periphery of the annular cavity 145 to a radius of an outer diameter of the central frame 130 may be about 1.25, 1.5, 1.75, 2.0, 2.25, 2.5, 2.75, 3.0, 3.25, 3.5, 3.75, 4.0, 4.25, 4.5, or at least about 5.0.

Figure 4:
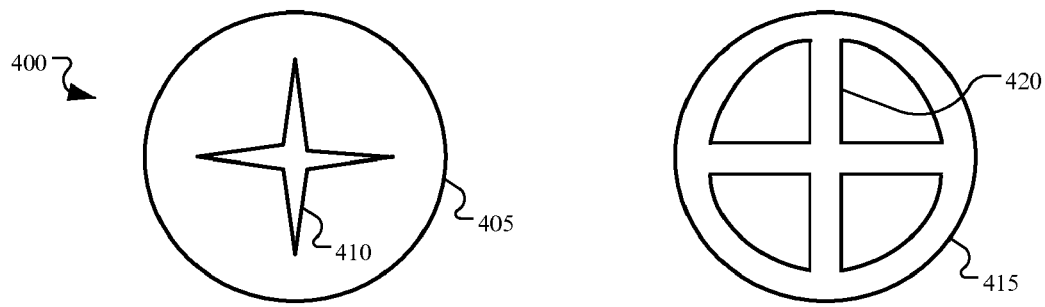
FIGS. 4-6 depict sets of exemplary valve membranes and corresponding membrane platforms.

Another exemplary embodiment of the valve system 140 is described, for example, with reference to FIG. 4 of U.S. Pat. No. 5,160,322 to Scheremet, et al., entitled "Occlusive Chest Sealing Valve," as issued Nov. 3, 1992.

In the depicted example, the valve membrane 155 rests on the membrane support member 150 and lies substantially in a plane. In some other embodiments, the support member 150 may be formed as a curved (e.g., concave, convex) surface.

Figure 3A:
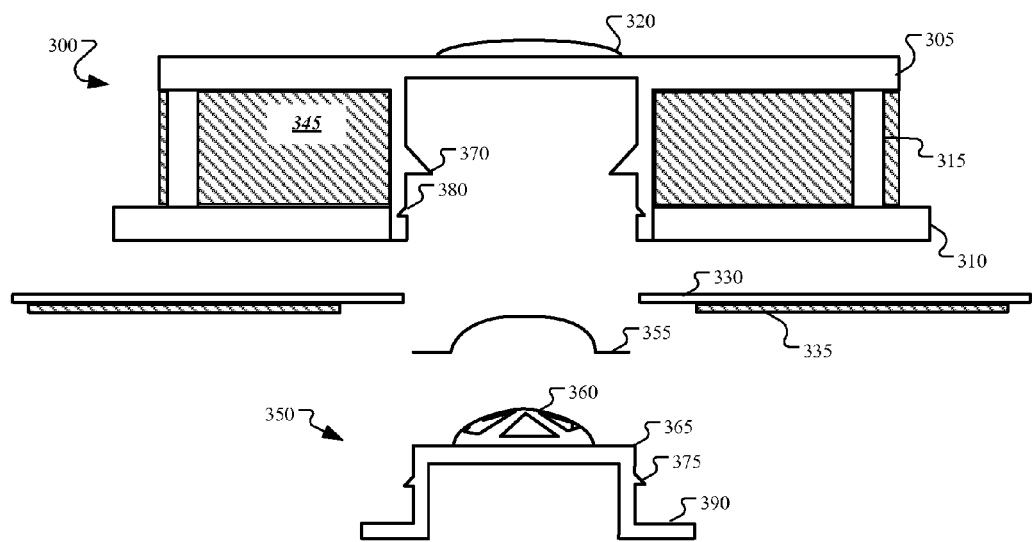
FIGS. 3A-3B depict cross-sectional exploded and assembled side views of an exemplary thoracic wound seal assembly.
Figure 3B:
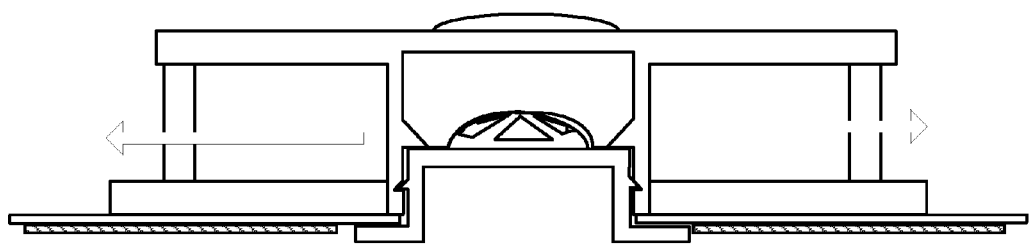

FIGS. 3A-3B depict cross-sectional exploded and assembled side views of an exemplary thoracic wound seal assembly. This embodiment depicts an exemplary valve support member having a curved surface.

FIG. 3A shows an exemplary wound seal assembly 300 that includes a base 305, a carrier 330, and a valve assembly 350. When assembled, as shown in FIG. 3B, these components form an embodiment of a thoracic wound seal.

The base 305 includes a base flange 310, supports 315, and a lens 320. The supports 315 form an annular cavity 345 in the space between the base flange 310 and an upper portion of the base 305, outside of a central portion configured to receive the valve assembly 350.

The carrier 330 is formed of a soft, pliable material that can provide a substrate for an adhesive layer 350 on one surface. In various embodiments, the adhesive 350 may be selectively applied to the carrier 330, for example, outside of the portion that makes contact with the valve assembly 350. In various implementations, the adhesive 335 may include a hydrogel to provide a substantially air tight seal to the patient's skin.

In various embodiments the carrier may be sufficiently soft and pliable to resist forming air channels when the patient's skin moves, or when initially applied to non-planar skin features. A sufficiently thick layer of hydrogel may advantageously conform substantially to the patient's body to allow the valve assembly 350 to maintain a substantial seal around the wound site.

In some embodiments, the hydrogel may include or be modified to include at least one anti-microbial agent to protect the patient against infection. In some examples, the anti-microbial agent may include a silver-containing compound (e.g., salt of silver).

The valve assembly 350 receives a valve membrane 355 disposed on a curved membrane support 360, which has apertures through which exudates and gasses may flow from the wound to the annular cavity 345. The membrane support 360 rests on a valve base 365, which has a cylindrical shape. On a perimeter of the valve base 365 is disposed a ring 375 and a valve flange 390.

In the base 305, the central portion to receive the valve assembly 350 includes, in this embodiment, a locating ring 370 to provide a vertical stop that locates the valve assembly 350 within the central portion. The central portion further includes a recess 380.

To assemble the wound seal assembly 300, as shown in FIG. 1B, the carrier 350 is captured between the base flange 310 and the valve flange 390. The valve membrane 355 is captured along its perimeter between the locating ring 370 and the valve base 365. The valve assembly 350 may be retained in position upon insertion when the ring 375 engages the corresponding recess 380. The valve assembly 350 may snap into place upon insertion such that a perimeter of the valve membrane 355 is held in compression.

The assembled wound seal assembly 300 permits unidirectional fluid flow from the wound, through the valve assembly 355. Fluids may then be discharged laterally through the annular cavity 345 in any radial direction out of the base 305.

Operation of the perimeter-capture membrane will next be further described with reference to the embodiments depicted in FIGS. 4-6.

Figure 5:
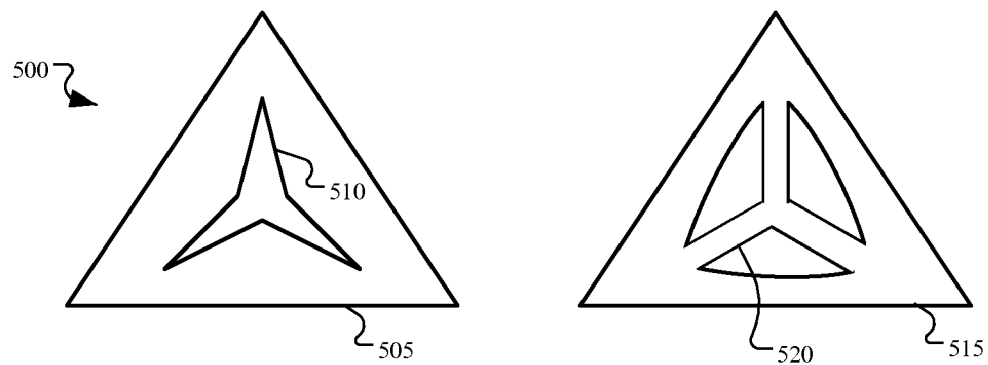
Figure 6:
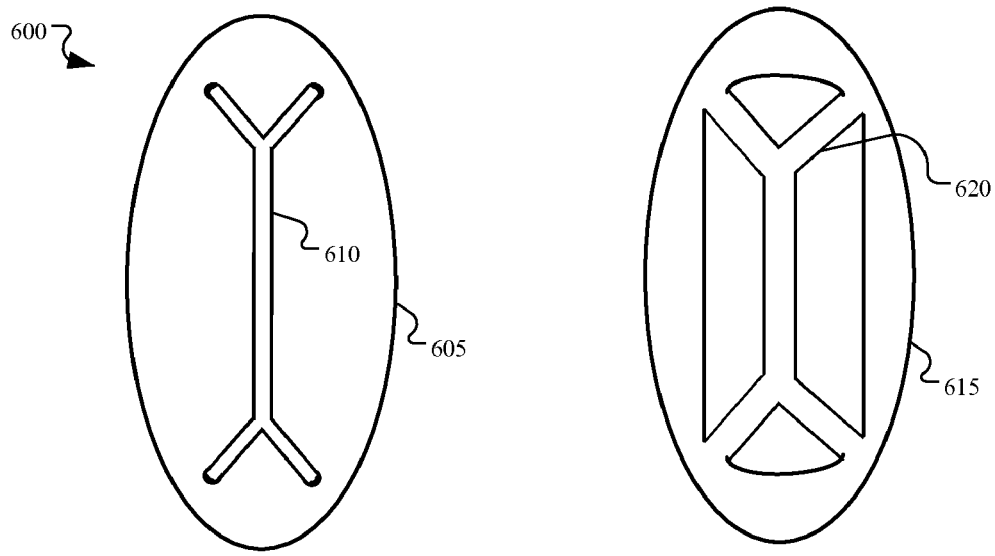

FIGS. 4-6 depict sets of exemplary valve membranes and corresponding membrane platforms. As shown in FIGS. 3A-3B, the perimeter of these valve membranes are captured and thus securely located. The embodiments of FIGS. 4-6 may be implemented in a planar (flat) support member (e.g., see membrane support member 150) or on a support member with a curved surface (e.g., see membrane support member 360). It is speculated by the inventors that a curved surface may be advantageous in yielding a reduced tendency for the membrane to become clogged, and there may be further advantages in sensitivity to releasing small pressures in the thoracic cavity, perhaps associated with the increased length of the aperture on a curved surface relative to a similar circumference valve in a planar format.

A valve embodiment 400 includes a membrane 405 with a single aperture 410. The aperture may be formed, for example, by cutting two crossed slits in a membrane. The membrane 405 is assembled on a valve base 415 so that the slits of the aperture 410 register along the corresponding membrane supports 420.

In operation, the valve responds to fluid pressure from the wound side (below the valve seal 415) by at least a portion of the membrane along the aperture 410 separating from the membrane support 420, permitting fluid to flow through the aperture. In response to fluid pressure from the atmospheric side, the valve assembly blocks reverse flow as the edges of the aperture 410 are in pressed in intimate contact with the membrane supports 420.

Similarly, FIGS. 5 and 6 depict exemplary valve embodiments 500, 600 in triangular and elliptical shapes, with membranes 505, 605 having apertures 510, 610, respectively. The membranes 505, 605 may be assembled on a valve base 515, 615 so that the slits of the aperture 510, 610 register along the corresponding membrane support structures 520, 620, respectively.

Figure 7A:
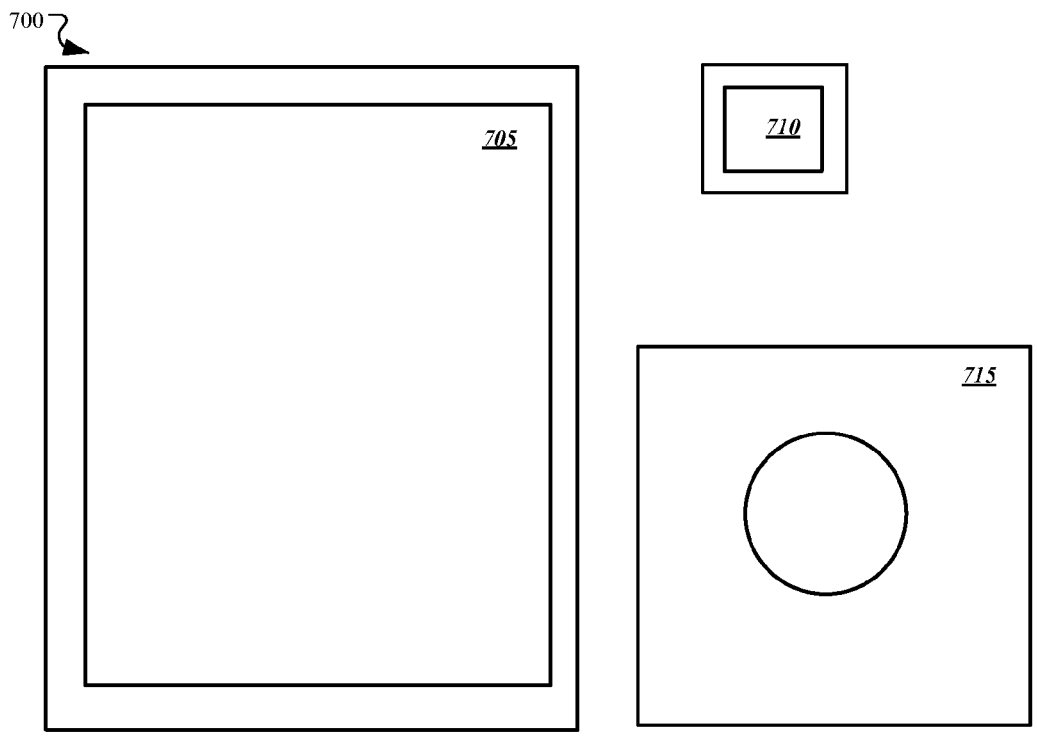
FIGS. 7A-7B depict plan views of exemplary kit for packaging an exemplary valve system.
Figure 7B:
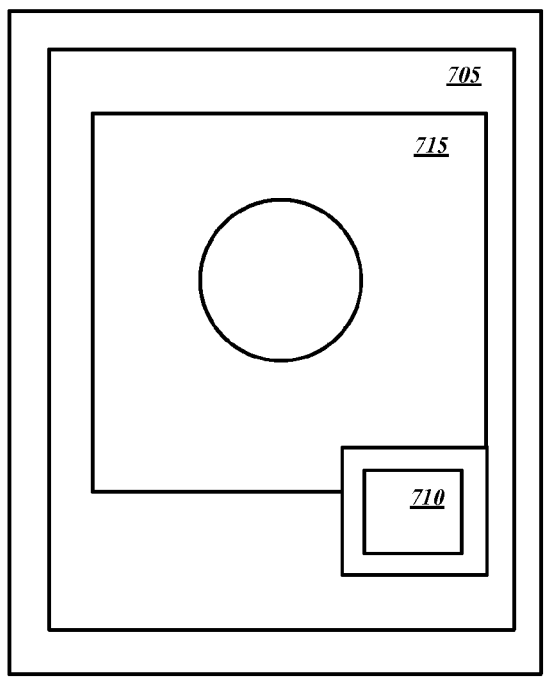

FIGS. 7A-7B depict plan views of an exemplary kit for packaging an exemplary valve system. It may be advantageous in some applications to have a kit 700 that includes a protective package 705, a pre-moistened anti-septic and/or anti-microbial wipe 710, and a thoracic wound seal 715. In some embodiments, the thoracic wound seal 715 may include a release liner to protect the hydrogel adhesive until ready for use. In some implementations, the packaging 705 may serve as a release liner directly, which may reduce the materials and/or manufacturing cost and further reduce the waste stream, for example.

In some implementations, the package 705 may have a foil backing on at least one or both sides. The package 705 may be vacuum sealed to substantially reduce or prevent ingress and/or egress of moisture or contaminants. A vacuum seal may advantageously extend the service life of the hydrogel, for example. In some examples, the kit may include a window on the package 705 to permit inspection of the contents. In some embodiments, the kit 700 may be rolled into a substantially cylindrical form for compact storage (e.g., in a medical bag).

Although various embodiments have been described with reference to the figures, other embodiments are possible. For example, portions of the housings 105, 110 may be coated with active materials, such as anti-microbials (e.g., silver). Some portions of the valve, such as the valve membrane and/or the interior surfaces of the valve housing may be partially or completed coated with a lubricious material to promote the flow of exudates, which may reduce the risk of occlusion of valve pathways.

Some embodiments of the valve assembly may omit the lens. In some applications, this may permit use of stronger, thinner plastic materials. In some examples, omission of the lens may permit a lower profile, which may be more comfortable when the patient lays down on the side with the valve assembly. Lower profiles may also permit the valve cavity to be enlarged to accommodate larger wounds.

In some implementations, it may be advantageous to provide a bandage or wound seal without the valve assembly. For example a wound seal may be formed of a carrier, a hydrogel, and an anti-microbial agent included in the hydrogel. The hydrogel may be stored between the carrier and a release liner that can be rapidly removed when needed for use as a wound dressing.

In various embodiments, the membrane may have visual indicia to make it easier to detect operation of the membrane that may be associated with pressure release from the thoracic cavity. In some examples, the membrane itself may be tinted yellow to distinguish it from the other substances that may be present in the valve (e.g., blood). The membrane may have dots, stripes, or other variations in color or markings to help the observer readily distinguish and identify the membrane through the lens, and to verify correct operation of the valve membrane, for example.

In some embodiments, such as those described with reference to FIGS. 3A-3B, means for attaching the carrier 300 to the base 305 include a compressive interference between the valve flange 390 and the base flange 310. In another embodiment, the valve flange 390 may be configured with a number of plastic posts that penetrate the carrier 330; in assembly, the posts may be transformed (e.g., by ultrasonic welding or heat staking process) into a shape or form (e.g., rivet head) that retains the carrier 330.

A number of implementations have been described. Nevertheless, it will be understood that various modification may be made. For example, advantageous results may be achieved if the steps of the disclosed techniques were performed in a different sequence, or if components of the disclosed systems were combined in a different manner, or if the components were supplemented with other components. Accordingly, other implementations are contemplated within the scope of the following claims.

What is claimed is:

1. A thoracic valve seal system, comprising:
   a carrier layer formed of a substantially pliable sheet material;
   an adhesive material on one surface of the carrier layer;
   a valve that permits fluid to flow through the valve in substantially only one direction;
   a housing that couples to the carrier layer and that, when sealed around a wound by the adhesive on the carrier layer, supports the valve in an orientation relative to the patient's body to permit fluids to flow substantially only from the wound to a region outside of the body, the housing comprising:
      a bottom housing that includes a sealing cavity to provide fluid communication from the wound to the valve when sealed around the wound; and,
      a top housing that couples to the bottom housing, wherein the top housing includes a flange that extends radially around a periphery of the valve to form an annular space between the top housing and the bottom housing.

2. The system of claim 1, wherein the adhesive comprises a hydrogel.

3. The system, of claim 2, wherein the adhesive material further comprises an ingredient with an effective amount of an anti-microbial agent.

4. The system of claim 1, wherein the valve comprises a flexible membrane.

5. The system of claim 1, further providing an annular coupling from the housing to a periphery of the flexible membrane.

6. The system of claim 1, wherein the top housing and the bottom housing include a plurality of interference fit features to mate to each other.

7. The system of claim 1, wherein the top housing and the bottom housing include a plurality of interference fit features extending between the top and the bottom housing to mate to each other and to couple the housing to the carrier layer.

8. The system of claim 1, wherein the provided housing forms an aperture that provides fluid communication from an exhaust side of the valve to the annular space between the top housing and the bottom housing.

9. The system of claim 8, further comprising a cavity to provide fluid communication through the apertures in a plane substantially parallel to a plane tangent to the wound.

10. The system of claim 1, wherein the top housing further comprises a lens to magnify an image of the valve.

11. A method of treating a thoracic puncture wound, the method comprising:
   providing a carrier layer formed of a substantially pliable sheet material;
   providing an adhesive material on one surface of the carrier layer;
   providing a valve that permits fluid to flow through the valve in substantially only one direction;
   providing a housing that couples to the carrier layer and that, when sealed around a wound by the adhesive on the carrier layer, supports the valve in an orientation relative to the patient's body to permit fluids to flow substantially only from the wound to a region outside of the body, the housing comprising:
   a bottom housing that includes a sealing cavity to provide fluid communication from the wound to the valve when sealed around the wound; and,
   a top housing that couples to the bottom housing, wherein the top housing includes a flange that extends radially around a periphery of the valve to form an annular space between the top housing and the bottom housing.

12. The method of claim 11, wherein the adhesive comprises a hydrogel.

13. The method of claim 12, wherein the adhesive material further comprises an ingredient with an effective amount of an anti-microbial agent.

14. The method of claim 11, wherein the valve comprises a flexible membrane.

15. The method of claim 11, further providing an annular coupling from the housing to a periphery of the flexible membrane.

16. The method of claim 11, further providing the top housing and the bottom housing include a plurality of interference fit features to mate to each other.

17. The method of claim 11, wherein the top housing and the bottom housing include a plurality of interference fit features extending between the top and the bottom housing to mate to each other and to couple the housing to the carrier layer.

18. The method of claim 11, wherein the provided housing forms a plurality of apertures that provide fluid communication from an exhaust side of the valve to the annular space between the top housing and the bottom housing.

19. The method of claim 11, further comprising providing a lens in the top housing to magnify an image of the valve.

20. The method of claim 11, further comprising providing a yellow tint on the membrane.

* * * * *